United States Patent [19]

Miyajima et al.

[11] Patent Number: 4,710,313

[45] Date of Patent: Dec. 1, 1987

[54] DETERGENT COMPOSITION FOR CONTACT LENSES

[75] Inventors: Nobuyuki Miyajima; Kenji Hata, both of Tokyo; Junichi Nakayama, Chiba, all of Japan

[73] Assignees: Lion Corporation, Tokyo; Toyo Contact Lens Co., Ltd., Nagoya, both of Japan

[21] Appl. No.: 873,351

[22] Filed: Jun. 12, 1986

[30] Foreign Application Priority Data

Jun. 26, 1985 [JP] Japan ................... 60-139799

[51] Int. Cl.$^4$ ............ C11D 7/32; C11D 7/42
[52] U.S. Cl. .................. 252/105; 252/174.12; 252/544; 252/546; 252/DIG. 12; 252/DIG. 14; 514/839
[58] Field of Search ............ 134/42; 252/105, 544, 252/174.12, DIG. 12, DIG. 14, 546; 514/839; 424/94

[56] References Cited

U.S. PATENT DOCUMENTS

| | | | |
|---|---|---|---|
| 3,741,901 | 6/1973 | Ziffer .................. | 252/105 |
| 3,983,002 | 9/1976 | Ohya et al. ........... | 435/209 |
| 4,195,974 | 4/1980 | Kothe et al. .......... | 8/138 |
| 4,285,738 | 8/1981 | Ogata ................. | 134/26 |
| 4,404,115 | 9/1983 | Tai ................... | 252/135 |
| 4,443,355 | 4/1984 | Murata et al. ......... | 252/174.12 |
| 4,609,493 | 9/1986 | Schäfer ............... | 252/546 |
| 4,610,800 | 9/1986 | Durham et al. ......... | 252/174.12 |

FOREIGN PATENT DOCUMENTS

| | | |
|---|---|---|
| 93784 | 11/1983 | European Pat. Off. |
| 209713 | 12/1983 | Japan . |
| 963 | 11/1979 | PCT Int'l Appl. . |
| 2088581 | 6/1982 | United Kingdom . |

*Primary Examiner*—Prince E. Willis
*Attorney, Agent, or Firm*—Burns, Doane, Swecker & Mathis

[57] ABSTRACT

This invention provides a detergent composition by which proteinaceous depositions can be easily removed from contact lenses in a short time, and method for removing such depositions from the contact lenses. The detergent composition comprises (A) at least one glycosidase selected from the group consisting of amylase, cellulase, pectinase, hemicellulase, alginase, heparinase and dextranase; and (B) at least one activator selected from the group consisting of urea, thiourea, acid salts of guanidine, reductants, amino acids and salts thereof.

3 Claims, No Drawings

DETERGENT COMPOSITION FOR CONTACT LENSES

BACKGROUND OF THE INVENTION (1) Field of the Invention

This invention relates to a detergent composition for contact lenses, in particular a detergent composition which is useful for removing proteinaceous depositions or retentions from contact lenses. This invention also relates to a method of removing such depositions and retentions from contact lenses.

(2) Description of the Prior Art

Among contact lenses, there are hard contact lenses composed primarily of methyl methacrylate, soft contact lenses comprising 2-hydroxy methacrylate, and N-vinyl pyrolidone or silicone contact lenses which are made by subjecting the surface of a hydrophobic material made from polysiloxane series to an electrical discharge in order to make its surface hydrophilic. Since, in particular, soft contact lenses and silicone contact lenses are flexible, good in oxygen permeability and since they can easily be fitted when these lenses are on the eyes, these lenses are widely used nowadays.

When such flexible contact lenses are worn for a long time, lipid, protein, mucin in tear and bacteria are deposited on the surface and into the mass thereof. Those depositions make the lenses opaque and also injure the eye.

Lipid deposited on the surface of a contact lens can be removed therefrom almost completely by detergents containing a surfactant as the main component and said detergents are generally used for this purpose. They do not, however, remove proteinaceous and mucinic depositions. In particular, boiling and sterilization of the contact lens further modifies the protein, causing it to coagulate so that the protein becomes strongly fixed to the lenses. As a result, the life of the lens is shortened.

There have been known detergents comprising protease and hydrosulfohydryl compound for cleaning contact lenses deposited with protein and mucin. These detergents are effective in cleaning such lenses but have a weak point in that a long time is required for cleaning. There have also been known detergents prepared by adding at least one compound selected from urea and guanidine hydrochloride salt to said detergents in order to shorten the cleaning time. However, such shortening effect is not altogether satisfactory.

SUMMARY OF THE INVENTION

Under such circumstances, the present inventors made a deep study of removal of dirt comprising mainly protein and mucin firmly attached to contact lenses (this dirt is hereinafter referred to as proteinaceous depositions), and they found a combination of a specific enzyme and a specific activator by which such proteinaceous depositions can be easily removed from the contact lenses in a short time.

It is, therefore, a primary object of the present invention to provide a detergent composition for contact lenses by which proteinaceous depositions can be removed from the contact lenses in a short time.

Another object of this invention is to provide a method effective in removing such depositions from the contact lenses.

These and other objects of this invention will be clear from the following description.

In accordance with the present invention, there is provided a detergent composition used for cleaning contact lenses, which comprises (A) at least one glycosidase selected from the group consisting of amylase, cellulase, pectinase, hemicellulase, alginase, heparinase and dextranase; and (B) at least one activator selected from the group consisting of urea, thiourea, acid salts of guanidine, reductants, amino acids and salts thereof.

The invention also provides a method from removing proteinaceous depositions from the contact lenses using such a detergent composition.

DESCRIPTION OF THE PREFERRED EMBODIMENTS

Examples of amylase of component (A) usable in the present invention include α-amylase, β-amylase, glucoamylase and isoamylase. Among these amylases, it is particularly preferable to use glucoamylase. These amylases can be easily obtained as commerical products, for example Glucotyme ® (by Nagase & Company, Ltd.), Morotomin Y ® (by Tanabe Seiyaku Co., Ltd.), Kokulase ® (by Sankyo Company Ltd.), Gluczyme AF-6 (by Amano Pharmaceutical Co., Ltd.).

Cellulase usable in this invention can be produced from fungi such as *Trichoderma viride, Aspergillus niger* or *Fusarium moniliforme.* These cellulases can easily be obtained as commerical products, typical of which are: Celluclast ® (by Novo Industri Japan LTD.), Dolicelaze ® (by Kyowa Hakko Kogyo Co., Ltd.), Cellulase AP-4 ® (by Amano Pharmaceutical Co., Ltd.), Meicelase (by Meiji Seika Kaisha Ltd.), Cellulase <Nagase> ® (by Nagase & Company, Ltd.) and the like.

Pectinase usable in this invention can be produced from a microorganism such as *Sclerotinia libertiana, Aspergillus niger, Coniothyrium diplodieulls,* etc. These pectinases can also be easily obtained as commercial products, examples being: Pectinase <Tanabe> ® (by Tanabe Seiyaku Co., Ltd.), Sclase-S ® (by Sankyo Company Limited), Pectinase <Toyo> ® (by Toyojozo Co., Ltd.), Cellulosin PC-8 ® (by Ueda Chemical Industrial Co., Ltd.), Pectinase G ® (by Amano Pharmaceutical Co., Ltd.) and Ultrazym 100 (by Novo Industri Japan LTD.). These pectinases can be preferably used in the present invention.

As for hemicellulase usable in this invention, there can be used Cellulosin HC ® (by Ueda Chemical Industrial Co., Ltd.), Cellulase A3 ® (by Amano Pharmaceutical Co., Ltd.), Gamanase 1.5L ® (by Novo Industri Japan LTD.), etc.

Furthermore, regarding the alginase, there can be used enzymes produced by Alginovibrio, Alginomonas, Alginobacter or the like.

As for the heparinase, there can be used enzymes obtained from culture of *Flavobacterium heparicum* or extracted from liver of cow, rabbit or mouse.

As for dextranase, there can be used enzymes produced by filamentous fungi such as Penicillium, Aspergillus, Verticillium or Spicaria.

In the detergent composition of the present invention, the amount of the glycosidase of component (A) is ordinarily 0.005 to 10% by weight (herafter referred to as %), preferably 0.05 to 5%.

Examples of acid salts of guanidine of component (B) usable in the present invention include guanidine hydrochloride and guanidine hydrobromide.

In the detergent composition of the present invention, there can be used many kinds of reductants, for example sulfites, bisulfites, dithionites, boron hydride salts, water-soluble mercapto compounds, and the like. It is preferable to use sulfurous acid alkali metal salts, hydrogen sulfurous acid alkali metal salts, sodium boron hydride, cysteine, cysteine hydrochloride, dithiothreitol, dithioerythritol or 1-thioglycerin. There can be also used many kinds of amino acids or salts thereof, whereas it is preferable to use DL-aspartic acid, sodium DL-aspartate, L-glutamic acid, glycine, DL-alanine, L-glutamine, cysteine hydrochloride, beside the above-described cysteine.

Urea, thiourea, acid salts of guanidine, reductants and amino acids of component (B) can be used singularly or in combination in the present invention. The amount of component (B) in the detergent is ordinarily 0.01 to 20%, preferably 0.1 to 10%. In addition, it is desirable that the weight ratio of the amount of component (B) to those of component (A) be 1/99 to 99/1, preferably 1/9 to 9/1.

Since the detergent composition of the present invention essentially comprises component (A) and (B), it is assumed that component (B) puts the glycosidase of component (A) in an active state so that it effectively attacks dirt of contact lenses, i.e. dirt in which many kinds of dirts are bound with a binder made from modification of a mixture of lipid, protein and mucin in tear. As a result, there can be obtained a good effect in removing such dirt from the contact lenses.

Beside components (A) and (B), suitable buffering agents and stabilizing agents can be added to the detergent composition of the present invention. For example, sodium citrate, potassium citrate, citric acid, boric acid, disodium edetate, various mixtures of phosphate buffering agents, sodium bicarbonate or the like can be added thereto. The amount of such buffering agents and stabilizing agents added is from about 0.001 to about 2.5%, preferably from about 0.01 to 1%. Furthermore, neutral inorganic salts can be added in an amount of 0.5 to 1.5% to the detergent composition in order to make the solution substantially isotonic. It is preferable that 0.8 to 1.0% by weight of sodium chloride, the main component of tear, be added thereto.

The formulation of the detergent composition of the present invention can take the form of a liquid which contains an aqueous medium and it also can take the form of a powder or solid. For making the detergent composition of the present invention in the form of a powder or solid, lubricants, binders and shaping agents can be added to the detergent composition. Among these agents are included glycerine, sorbitol, propylene glycol, polyethylene glycol, dextrane, methyl cellulose, hydroxyethyl cellulose, aqueous soluble salts of carboxymethyl cellulose or natural hydrophilic compounds such as gelatine, alginates, tragacanth, pectin, gum arabic, and soluble starches. These agents can be used in the amount of 0.01 to 10%, preferably 0.1 to 5%. In addition, to the detergent composition of this invention is added other enzymes than the glycosidase specified as the component (A).

The method of use of the detergent composition of the present invention is as follows: First, there is prepared an aqueous solution containing an effective cleaning amount, for example between 0.02 to 60%, preferably 0.2 to 40% by weight, of such a detergent composition. In particular, it is generally better for the aqueous solution to contain 0.01-50% of component (A) and 0.05-10% of component (B), preferably 0.1-20% of the former and 0.1-10% of the latter. The pH of these solutions is ordinarily 2 to 11, preferably 3 to 8.

Thereafter, the contact lenses are removed from the wearer's eyes and put into said solution. The lenses are allowed to soak for a period of about 1 minute to about 24 hours at a temperature of, for example, 0° to 100° C. Soaking in a heated solution improves detergency.

The present invention now will be further illustrated by the following examples.

EXAMPLE 1

0.3 g of cellulase (Cellulosin PC-8 ®: Ueda Chemical Industrial Co., Ltd.), 0.5 g of urea, 0.05 of sodium chloride, 0.02 g of citric acid, 0.003 g of trisodium citrate and 0.005 g of disodium edetate were put in a plastic container, after which water was added to bring the total amount to 10 ml. A dirty soft contact lens which had been used for 6 months was soaked in the solution for about 3 hours at room temperature and then the lens was taken out and simply washed with water. It was then soaked in physiologic saline for an hour. As a result, a cleaned lens was obtained.

EXAMPLE 2

0.1 g of water-soluble pectinase (Pectinase Tanabe ®: Tanabe Seiyaku Co., Ltd.), 0.3 g of thiourea, 0.02 g of acetic acid, 0.07 g of sodium chloride and 0.01 g of sucrose were put in a plastic container, after which water was added to bring the total amount to 10 ml. Cleaning was conducted by the same procedure as described in EXAMPLE 1, whereby a cleaned lens was obtained.

EXAMPLE 3

0.08 g of hemicellulase (Cellulosin HC ®: Ueda Chemical Industrial Co., Ltd.), 0.1 g of 1-thioglycerin, 0.03 g of citric acid, 0.05 g of sodium acetate, 0.01 g of disodium edetate and 0.02 g of polyethylene glycol (average molecular weight: 4,000) were put in a plastic container, after which water was added to bring the total amount to 10 ml. Cleaning was conducted by the same procedure as described in EXAMPLE 1, whereby a cleaned lens was obtained.

EXAMPLE 4

0.05 g of amylase (Gluczyme AF-6 ®: Amano Pharmaceutical Co., Ltd.), 0.04 g of DL-aspartic acid, 0.01 g of citric acid, 0.02 g of trisodium citrate, 0.003 g of disodium edetate and 0.002 g of sodium chloride were put in a plastic container, after which water was added to bring the total amount to 10 ml. Cleaning was conducted by the same procedure as described in EXAMPLE 1, whereby a cleaned lens was obtained.

EXAMPLE 5

0.2 g of cellulase (Cellulase Nagase ®): Nagase & Company, Ltd.), 0.01 g of L-cysteine, 0.05 g of urea, 0.05 g of acetic acid, 0.01 g of trisodium citrate and 0.01 g of glucose were put in a plastic container, after which water was added to bring the total amount to 10 ml. Cleaning was conducted by the same procedure as described in EXAMPLE 1, whereby a cleaned lens was obtained.

EXAMPLE 6

0.2 g of amylase (Morotomin Y ®: Tanabe Seiyaku Co., Ltd.), 0.1 g of guanidine hydrochloride, 0.005 g of disodium edetate, 0.01 g of citric acid and 0.08 g of sodium chloride were put in a plastic container, after which water was added to bring the total amount to 10 ml. Cleaning was conducted by the same procedure as described in EXAMPLE 1, whereby a cleaned lens was obtained.

EXAMPLE 7

0.1 g of alginase prepared from culture of Alginomonas (soil bacteria), 0.15 g of guanidine hydrobromide, 0.01 g of sodium carbonate, 0.01 g of disodium edetate and 0.1 g of sodium chloride were put in a plastic container, after which water was added to bring the total amount to 10 ml. Cleaning was conducted by the same procedure as described in EXAMPLE 1, whereby a cleaned lens was obtained.

EXAMPLE 8

Cleaning was conducted by the same procedure as described in EXAMPLE 1, except that 0.15 g of heparinase obtained from culture of *Flavobacterium heparicum* (microorganism), 0.25 g of urea, 0.001 g of boric acid, 0.01 g of disodium edetate and 0.05 g of sodium chloride were used. As a result, a cleaned lens was obtained.

EXAMPLE 9

Cleaning was conducted by the same procedure as described in EXMAPLE 1, except that 0.2 g of dextranase (produced by Sankyo Company Limited), 0.1 g of dithiothreitol, 0.01 g of disodium edetate, 0.05 g of sodium citrate and 0.09 of sodium chloride. As a result, a cleaned lens was obtained.

As is obvious from the above description, according to the present invention, proteinaceous depositions can easily be removed from the contact lenses in a short time.

What is claimed is:

1. A detergent composition used for cleaning contact lenses, which comprises 0.005 to 10% by weight of (A) at least one glycosidase selected from the group consisting of cellulase, pectinase, and hemicellulase; 0.01 to 20% by weight of (B) at least one activator selected from the group consisting of urea, thiourea, amino acids and salts thereof, sulfurous acid alkali metal salts, hydrogen sulfurous acid alkali metal salts, thioglycerin, dithiothreitol and dithioerythritol and the balance being water.

2. A detergent composition as set forth in claim 1, wherein the component (A) in hemicellulase.

3. A detergent composition as set forth in claim 1 wherein the amount of the component (A) is 0.05 to 5% by weigth and the amount of the component (B) is 0.01 to 10% by weight.

* * * * *